United States Patent
Boegershausen et al.

(10) Patent No.: US 10,307,945 B2
(45) Date of Patent: Jun. 4, 2019

(54) PROCESS OR THE MANUFACTURE OF IMPLANTS OR INTERMEDIATE PRODUCTS OF SUCH IMPLANTS AS WELL AS IMPLANTS AND INTERMEDIATE PRODUCTS OBTAINED BY SUCH PROCESS

(71) Applicant: Polytech Health & Aesthetics GmbH, Dieburg (DE)

(72) Inventors: Oliver Boegershausen, Darmstadt (DE); Patrick O'Leary, Babenhausen (DE)

(73) Assignee: POLYTECH HEALTH & AESTHETICS GMBH, Dieburg (DE)

(*) Notice: Subject to any disclaimer, the term of this patent is extended or adjusted under 35 U.S.C. 154(b) by 484 days.

(21) Appl. No.: 13/650,975

(22) Filed: Oct. 12, 2012

(65) Prior Publication Data

US 2013/0096676 A1    Apr. 18, 2013

(30) Foreign Application Priority Data

Oct. 14, 2011 (EP) ..................... 11008322

(51) Int. Cl.
| | |
|---|---|
| B29C 41/14 | (2006.01) |
| B29C 41/40 | (2006.01) |
| A61F 2/12 | (2006.01) |
| B29C 44/06 | (2006.01) |
| B29C 41/20 | (2006.01) |

(52) U.S. Cl.
CPC ............. B29C 44/06 (2013.01); A61F 2/12 (2013.01); B29C 41/14 (2013.01); B29C 41/20 (2013.01)

(58) Field of Classification Search
CPC ......... B29C 44/06; B29C 41/14; B29C 41/20; A61F 2/12; A61F 2/441
See application file for complete search history.

(56) References Cited

U.S. PATENT DOCUMENTS

| | | | |
|---|---|---|---|
| 3,293,663 A | | 12/1966 | Cronin et al. |
| 3,366,975 A | * | 2/1968 | Pangman ................... 623/8 |
| 4,455,691 A | * | 6/1984 | Van Aken Redinger .................... A61F 2/12 428/447 |
| 4,681,587 A | | 7/1987 | Eberl et al. |
| 4,944,750 A | | 7/1990 | Cox, Jr. |
| 5,141,581 A | | 8/1992 | Markham |
| 5,296,069 A | | 3/1994 | Robert |
| 5,938,878 A | * | 8/1999 | Hurley ..................... A43B 5/08 156/219 |
| 2006/0235094 A1 | | 10/2006 | Habibi-Naini |
| 2009/0030515 A1 | * | 1/2009 | Schuessler et al. .............. 623/8 |
| 2010/0273011 A1 | * | 10/2010 | Zhong ....................... B32B 7/12 428/429 |
| 2011/0184531 A1 | * | 7/2011 | Goraltchouk et al. ..... 623/23.72 |
| 2011/0276135 A1 | * | 11/2011 | Yacoub et al. .................... 623/8 |
| 2012/0142798 A1 | * | 6/2012 | Thompson et al. .......... 521/154 |
| 2013/0164517 A1 | * | 6/2013 | Shope ....................... B32B 5/02 428/220 |

FOREIGN PATENT DOCUMENTS

| | | |
|---|---|---|
| FR | 2675049 A1 | 10/1992 |
| FR | 2677539 A1 | 12/1992 |
| GB | 2243324 A | 10/1991 |
| WO | 1990/000888 A1 | 2/1990 |
| WO | 2010045581 A1 | 4/2010 |
| WO | 2010/069019 A1 | 6/2010 |

OTHER PUBLICATIONS

Herman, The Meme Implant, Plast. Reconstr. Surg., 73(3):411-414 (1984).

Lilla et al., Long-term study of reactions to various silicone breast implants in rabbits, Plast. Reconstr. Surg., 57:637-649 (1976).

* cited by examiner

*Primary Examiner* — William P Bell

(74) *Attorney, Agent, or Firm* — Meunier Carlin & Curfman LLC

(57) ABSTRACT

Disclosed is a process for the manufacture of implants or intermediate products of such implants as well as implants and intermediate products obtained by such process. For example, the disclosed process can be used for the manufacture of breast implants, of implants for the thighs, buttocks and calves.

14 Claims, No Drawings

PROCESS OR THE MANUFACTURE OF IMPLANTS OR INTERMEDIATE PRODUCTS OF SUCH IMPLANTS AS WELL AS IMPLANTS AND INTERMEDIATE PRODUCTS OBTAINED BY SUCH PROCESS

BACKGROUND

In the manufacture of implants such as breast implants very high standards have to be met in a reproducible manner in terms of, for example, materials employed and processing details used. In addition, the dimension and the shape of an implant have to be obtained in a reliable manner within very narrow tolerances. Implants which do not meet such standards usually have to be discarded. Moreover, any suboptimal implant may increase the risk of non-compliance with the patient and may even be rejected by the tissue of such patient. In case a breast implant is not accepted by the surrounding tissue there is a very high likelihood of so-called capsular contracture, that is, a hard sphere of collagen is formed around the implant thereby necessitating additional surgery.

It is believed that capsular contracture is caused, among others, by small pieces which have been broken off or have become separated from the surface or the shell of the implant. Further, it has been postulated that by use of structured or textured implant surfaces capsular contracture can be repressed either completely or at least for much longer periods of time compared to other types of implants.

Therefore, much effort has been spent in optimizing both the surface structure and/or material of an implant as well as its manufacture.

In U.S. Pat. No. 5,296,069 a process for the manufacture of implants is disclosed whose surfaces are coated with an amorphous material which shall not come loose thereby preventing capsular contracture. This process requires disposing a first and a second sheet assembly on the front and the back side of an implant being already filled with gel, i.e. to a finished implant, and which has smooth surfaces. Said first sheet assembly and said second sheet assembly have to be made from a non-vulcanized silicone sheet and a foam sheet. It is required to pass said sheet assembly through two parallel and spaced apart rollers so as to exert a predetermined pressure for adhering said assembly. It is the non-vulcanized silicone sheet which in each case faces the smooth surface of the implant. Where the two sheets come together, they go out away from the implant; it is not possible for them to curl under the implant. The joint overlapping portions of said first and second sheet assemblies need to be cut off thereby generating a circumferential seam in that section of the implant which is bridging its front and the back side. It has been found that such seam may not be well accepted by the tissue of the patient. Moreover, the process according to U.S. Pat. No. 5,296,069 does not eliminate the problem of folds, wrinkles or even voids being formed on or between the assembly sheets and the underlying implant. This process is therefore rather cumbersome and inefficient.

In FR 2,675,049 A1, a breast prosthesis is described where a specific polyether polyurethane is glued onto a silicone envelope filled with a silicone gel. In a similar manner in FR 2 677 539 A1 a polyurethane sheet is glued to a breast implant being made of elastomeric silicone material. In order to minimize the risk of capsular contracture it is proposed to glue a first polyurethane sheet onto the front side of the implant and a second polyurethane sheet to the backside of said implant and to leave a circumferential area uncovered by said polyurethane sheets which bridges the front and the back side of said implant.

Although it has been proposed for about 30 years to make use of textured surfaces, e.g. in the form of polyurethane foams for breast implants in order to reduce the risk of capsular contracture—as evidenced by S. Herman, Plastic & Reconstructive Surgery, 1984, pages 411 to 414, and J. A. Lilla and L. M. Vistmis, Plastic & Reconstructive Surgery 1976, pages 637 to 649,—efforts are still ongoing to increase patient compliance, comfort and safety. For example, in WO 2010/069019 A1 breast implants are described having independent expandable and interactive compartments and which have an external silicone membrane which can externally be coated with a *Ricinus communis* polyurethane foam covered with hydroxyapatite microcrystals or nanocrystals.

Thus, there still is a need to provide a manufacturing process which in itself guarantees to obtain high quality products in a reliable and reproducible manner while yet yielding affordable products.

SUMMARY

Disclosed is a process for the manufacture of implants or intermediate products of such implants as well as implants and intermediate products obtained by such process. For example, the disclosed process can be used for the manufacture of breast implants, of implants for the thighs, buttocks and calves.

DETAILED DESCRIPTION

Disclosed is a process for manufacturing implants or intermediate products of such implants, in particular breast implants. The method comprises:

a) providing an implant shell comprising cured or uncured silicone, in particular having a front side, a back side and a region bridging said front and back side, b) optionally subjecting the uncured silicone of said implant shell to at least one curing step, in order to undergo complete or partial vulcanization, and applying at least one uncured additional silicone layer to the implant shell so obtained, in particular to the front side, the region bridging the front and back side and optionally also part of the back side which follows said bridging region, c) placing a first foam sheet over at least part of the uncured implant shell, in particular over the front side, the region bridging said front and back side and at least part of the back side of the implant shell, as provided in step a) or as obtained in step b), d) subjecting the implant shell obtained in step c) to at least one curing step in order to vulcanize the uncured silicone of step a) or the additional uncured silicone layer of step b) and, optionally, the silicone of the implant shell not cured yet, thereby bonding the first foam sheet to the implant shell, e) optionally removing excess foam sheet not bonded by curing in step d) to the back side of the implant shell, and f) applying at least one sheet comprising partially or completely uncured silicone to the back side of the implant shell, thereby in particular covering those parts not covered by the first foam sheet.

In the disclosed process, it is not a finished implant which already has been filled with gel that is covered with a foam sheet. Instead, it is the implant shell which is covered with a foam sheet.

The implant shell of step a) comprising uncured silicone in one embodiment can also be unfinished in that it represents an intermediate product still containing, in particular on its outer surface, uncured reaction sites.

The disclosed process can for example be used for the manufacture of breast implants, of implants for the thighs, buttocks and calves.

In some cases, the implant shell comprising uncured silicone, in particular being made of one or several layers of uncured silicone, is brought in contact with a first foam sheet. Usually, said foam sheet, e.g. a polyurethane foam sheet, is allowed to flow into the semi-liquid silicone surface of the implant, thereby surrounding each strand of the foam with silicone. The foam sheet can be pulled, pushed and/or stretched into the three dimensional shape of the implant thereby increasing the likelihood of avoiding folds or wrinkles. By subjecting said combined intermediate product to a curing step (step d)) the first foam sheet is tightly bonded to the implant shell. In other cases, the implant shell provided in step a) is first subjected to a curing step thereby arriving at a completely or partially vulcanized product to which subsequently an additional layer of uncured silicone is applied. In each case, an intermediate unit is formed wherein the first foam sheet has become an integral part of the implant shell. In case of destruction, foam particles as such can no longer be separated from said implant shell. Any risk of delamination is eliminated.

Another intermediate product can be obtained in that after process step f) another process step (step h)) is added which comprises subjecting the at least one sheet applied to the back side of the implant shell in step f) to curing so that it undergoes vulcanization, thereby in particular bonding said sheet to the back side of the implant shell. In some cases, the sheet has been obtained by applying an outer uncured silicone layer to a cured silicone sheet comprising one or several layers of silicone. These layers may have been cured in subsequent steps once a layer of uncured silicone has been formed. Alternatively, a set of uncured silicone layers can be cured as a whole before the additional uncured outer layer is applied. In some cases, the outer layer of uncured silicone is brought in contact with the silicone surface at the back side of the implant shell. In a subsequent step said sheet of step h) is cured so that it is tightly bonded to the back of the implant shell.

In some embodiments, the sheet applied in step f) in addition comprises at least one foam sheet (in the following also designated as second foam sheet), in particular at least one layer of polyurethane foam, as the outer layer of said sheet thereby forming a sheet assembly (in the following also referred to as first sheet assembly).

Another intermediate implant can be obtained in that after process step f) and prior to or after process step h) another process step (step g)) is added which comprises filling the implant shell with at least one gel, gelatinizable fluid or liquid. The silicone sheet or patch, which can be combined with the at least one second foam sheet or layer on its outside, can be used to stitch a needle therethrough. In this way gel, gelatinizable fluid or liquid is transferred in the implant shell. Once the needle is removed said sheet or patch is subjected to a curing step thereby allowing the silicone layer or sheet to vulcanize. In this manner it is not only possible to join the second foam layer in order to become an integral part of the sheet assembly, but it is also possible to tightly join the silicone layer to the back side of the implant, and to ensure that it is fluid-tight.

Accordingly, from process step g) an implant shell results which can be used as such for completing the manufacturing cycle, for example, by filling the implant shell with at least one gel, gelatinizable fluid or a liquid (step g)) or by subjecting the at least one sheet applied to the back side of the implant shell in step f) to curing so that it undergoes vulcanization thereby bonding said sheet to the back side of the implant shell.

Thus, a finished implant can be obtained by including after process step g) or after step h) the following process steps:

i) providing a third foam sheet, in particular at least one layer of polyurethane foam, or a second sheet assembly which comprises a sheet or layer comprising cured and/or uncured silicone, in particular uncured silicone, and at least one fourth foam sheet, in particular at least one layer of polyurethane foam, as the outer layer of said sheet assembly, and j) joining said third foam sheet, or said second sheet assembly via its silicone sheet or layer to the sheet of step f) and/or the back side of the implant shell.

In some instances the filled implant shell is subjected to a curing step, in particular to a thermal curing step (step k)) after process step g), h), i) and/or j), in particular if the gel, gelatinizable gel or the fluid shall be optimized thereby, e.g. in terms of consistency or durability.

The first sheet assembly can be obtained by a least one separate pressing and/or curing step, in particular comprising pressing between pressing plates, in particular plates having a temperature sufficiently high to initiate curing of the silicone sheet thereby also bonding the foam sheet thereto.

The second sheet assembly can best be obtained by a least one separate pressing step, in particular comprising pressing between pressing plates, in particular plates having a temperature which does not initiate curing of the silicone sheet.

The second sheet assembly when placed on the sheet of step f) and/or the back side of the implant shell and the gel, gelatinizable fluid or the liquid can be subjected to curing in one step, i.e. at the same time. In this manner the processing can be significantly alleviated.

It is also possible to place the filled implant shell into an external mold reflecting or having the desired shape of the individual implant prior to curing the material filled in the implant shell, and to subject the filled implant shell to a curing step when placed inside said mold.

The implant shell in step a) can be obtained by providing a mold to which layers of uncured silicone, either liquid as such and/or dissolved in a solvent, are applied in a stepwise manner, in particular comprising the at least partial evaporation of solvent. This mold can already have the shape of the finished implant. By such a mode of action the shape of the mold dictates the form of the implant. The mold can be held by a mandrel handle on its back side, which is responsible for a hole in the back side of the implant shell which needs to be covered with a sheet or patch as specified in process step f). The implant shell according to this variant can best be obtained by dipping or casting the mold in uncured silicone, either liquid as such and/or dissolved in a solvent, in a stepwise manner. That is, after a first dipping/casting step a rather sticky and viscous layer of uncured silicone is obtained, which in case dissolved silicone has been used still may contain some solvent. This process can also be described as multiple dip coating. Once a sufficient number of uncured silicone layers have been produced on the mold, it can be placed in an oven to undergo vulcanization. Alternatively, each uncured silicone layer is subjected to curing before another uncured silicone layer is added, e.g. by dipping and/or casting as described above. Hence, it is also possible that the implant shell of step a) is completely cured.

In particular, in case color shall be applied to the implant shell, at least one silicone layer that is not the outer silicone layer of the implant shell of step a), optionally the second but last silicone layer of said implant shell, can comprise at least one colorant and/or pigment, in particular titanium dioxide.

As with the formation of individual uncured silicone layers in step a), it is also possible to obtain the at least one additional silicone layer of step b) by dipping or casting the implant shell in uncured silicone, either liquid as such and/or dissolved in a solvent, whereupon said layer can be subjected to at least partial evaporation of the solvent thereby furnishing a layer of uncured silicone. This additional layer of uncured silicone can be sticky and viscous.

The first foam sheet can be placed in one piece over the entire front side, at least part of the region bridging the front and the back side and at least part of the back side of the implant shell. In this manner there are no seams, folds or wrinkles on the front side, on the region bridging the front and the back side and also on at least part of the back side. Thus, it is possible that the first foam sheet after having been placed on and bonded to the implant shell is free of seams and preferably also of folds on the front side as well as in particular on the region bridging the front and the back side of the implant shell. In particular case the implant shell is still on the mold said first foam sheet can be pressed and tightly fitted to the uppermost silicone layer.

The first, second, third and/or fourth foam sheet can comprise or be made of at least one polyurethane layer.

By applying step d) the foam sheet can become an integral part of the implant shell.

The excess first foam sheet not bonded by curing according to step d) on the back side of the implant shell can be cut off in step e).

The implant shell as obtained in step d) or in step e) can be taken from the mold, i.e. only after the first foam sheet has been applied to the implant shell. Evidently, with the disclosed process there is no direct need to employ an external mold, rather an internal mold can be used in one of its embodiments.

The disclosed process can further involve well known steps, such as sterilization, packing and labeling, that are typically needed to obtain a commercial product.

By relying on the disclosed process, surprising advantageous effects can be obtained. This process guarantees that there is no circumferential seam at that region of an implant which bridges its front and back sides. Implants can be obtained in a reliable manner based on the disclosed process, which do not contain voids, folds or wrinkles These implants also do not tend to delaminate.

Although modifications and changes maybe suggested by those skilled in the art, it is the intention of the applicant to embody within the patent warranted hereon all changes and modifications as reasonably and probably come within the scope of this contribution to the art. The features of the present disclosure which are believed to be novel are set forth in detail in the appended claims. The features disclosed in the description, the figures as well as the claims could be essential alone or in every combination for the realization of the disclosure in its different embodiments.

What is claimed is:

1. A method for manufacturing implants or intermediate products of such implants, comprising
    a) providing an implant shell having a front side, a back side and a region bridging said front and back side and comprising uncured silicone being made of and containing several layers of uncured silicone, wherein the implant shell is unfinished in that it represents an intermediate product having still uncured reaction sites that are on the outer surface of the implant shell and wherein the implant shell is obtained by providing a mold to which layers of uncured silicone are applied by dipping and/or casting in a stepwise manner without subjecting the uncured silicone layer to curing before another uncured silicone layer is added, wherein the uncured silicone is liquid as such and/or is dissolved in a solvent,
    b) placing a first foam sheet over at least part of the front side, the region bridging said front and back side and at least part of the back side of the uncured implant shell as provided in step a), wherein the first foam sheet is made of at least one polyurethane layer, wherein the first foam sheet is placed in one piece over the entire front side, at least part of the region bridging the front and the back side and at least part of the back side of the implant shell,
    c) subjecting the implant shell obtained in step b) to at least one curing step in order to vulcanize the uncured silicone of step a), thereby bonding the first foam sheet to the implant shell,
    d) optionally removing excess foam sheet not bonded by curing in step c) to the back side of the implant shell,
    e) applying at least one sheet comprising partially or completely uncured silicone to the back side of the implant shell, thereby covering those parts not covered by the first foam sheet, further comprising after step e) the process step,
    f) subjecting the at least one sheet applied to the back side of the implant shell in step e) to curing so that it undergoes vulcanization thereby bonding said sheet to the back side of the implant shell,
    further comprising after process step f) the process steps
    g) filling the implant shell with at least one gel, gelatinizable fluid, or a liquid, further comprising after process step a) the process steps
    h) providing a second foam sheet, or a first sheet assembly which comprises at least one third foam sheet as the outer layer of said first sheet assembly and a sheet or layer comprising cured and/or uncured silicone,
    i) joining said second foam sheet, or said first sheet assembly via its silicone sheet or layer to the sheet of step e) and/or the back side of the implant shell, and
    j) subjecting the filled implant shell, and optionally the uncured silicone layer of the first sheet assembly, to curing.

2. The method of claim 1, wherein the implant is a breast implant.

3. The method of claim 1, comprising at least partial evaporation of solvent and/or liquid of the implant shell of step a).

4. The method of claim 1, wherein at least one silicone layer which is not the outer silicone layer of the implant shell of step a) comprises at least one colorant and/or pigment.

5. The method of claim 4, wherein the pigment is titanium dioxide.

6. The method of claim 1, wherein the first foam sheet after having been placed on and bonded to the implant shell is free of seams on the front side as well as on the region bridging the front and the back side of the implant shell.

7. The method of claim 1, wherein the implant shell obtained in step c) or in step d) is taken from the mold.

8. The method of claim 1, wherein the second foam sheet is at least one layer of polyurethane foam.

9. The method of claim 1, wherein the third foam sheet is at least one layer of polyurethane foam.

10. The method of claim 1 wherein the curing in step i) is thermal curing.

11. The method of claim 1, wherein the sheet applied in step e) further comprises at least one fourth foam sheet as the outer layer thereby forming a second sheet assembly.

12. The method of claim 11, wherein the at least one fourth foam sheet is at least one layer of polyurethane foam.

13. The method of claim 12, wherein the second sheet assembly has been obtained by at least one pressing and/or curing step, and/or wherein the first sheet assembly has been obtained by a least one pressing step.

14. The method of claim 13, wherein the pressing step comprises pressing between pressing plates at a temperature which does not initiate curing of the uncured silicone.

* * * * *